United States Patent [19]

Lee

[11] Patent Number: 5,169,311

[45] Date of Patent: Dec. 8, 1992

[54] ORTHODONTIC BRACKET AND METHOD

[75] Inventor: Brian W. Lee, Victoria, Australia

[73] Assignee: Orthodontic Research Australia PTY. Limited, Victoria, Australia

[21] Appl. No.: 545,401

[22] Filed: Jun. 28, 1990

[51] Int. Cl.$^5$ ................................................ A61C 3/00
[52] U.S. Cl. ......................................... 433/14; 433/24
[58] Field of Search ...................... 433/8, 9, 14, 16, 24

[56] References Cited

U.S. PATENT DOCUMENTS

| | | | |
|---|---|---|---|
| 1,821,171 | 9/1931 | Atkinson | 433/14 |
| 3,163,933 | 1/1965 | Begg et al. | 433/14 |
| 3,445,933 | 5/1969 | Kesling | 433/14 |
| 3,660,900 | 5/1972 | Andrews | 433/16 |
| 3,975,824 | 8/1976 | Lee | 433/14 |
| 4,242,085 | 12/1980 | Wallshein | 433/14 |
| 4,561,844 | 12/1985 | Bates | 433/16 |
| 4,585,413 | 4/1986 | Wool | 433/15 |

*Primary Examiner*—John J. Wilson

*Attorney, Agent, or Firm*—Learman & McCulloch

[57] ABSTRACT

An orthodontic bracket and method of fitting is disclosed comprising a bracket of the type including a base portion adapted for attachment to the labial surface of a tooth:

(i) A lock pin receiving portion having a substantially vertical opening extending there through for the lock pin;

(ii) An arch-wire support portion extending substantially normal to the said vertical opening and being disposed between the opening and the base portion.

The bracket being adapted for adherence to a tooth and including a slot comprising an arch-wire support portion for receipt of a ribbon arch-wire of substantially rectangular cross-section adapted to be inserted gingivo-occlusally into the support portion, wherein the base of said support portion is angulated at specific preset angles between 0 to 20 degrees.

6 Claims, 3 Drawing Sheets

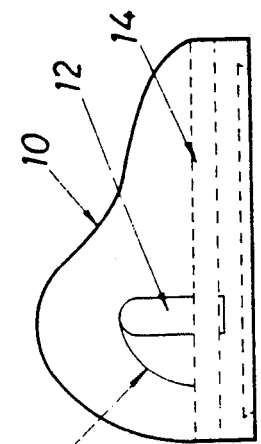
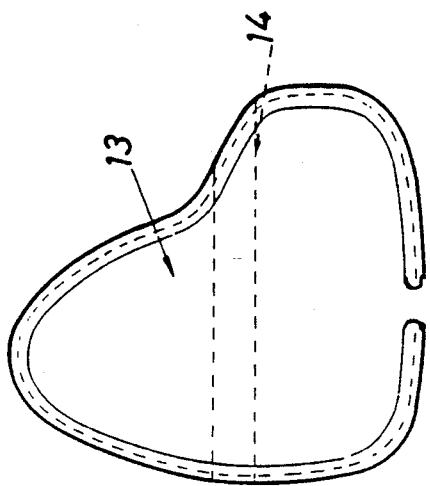
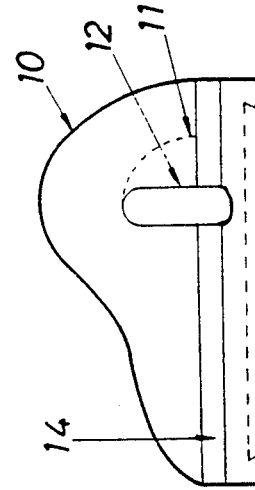
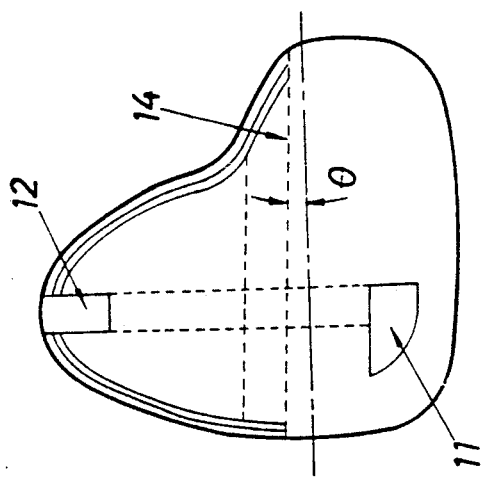
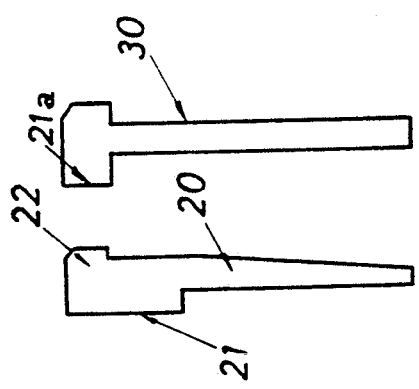
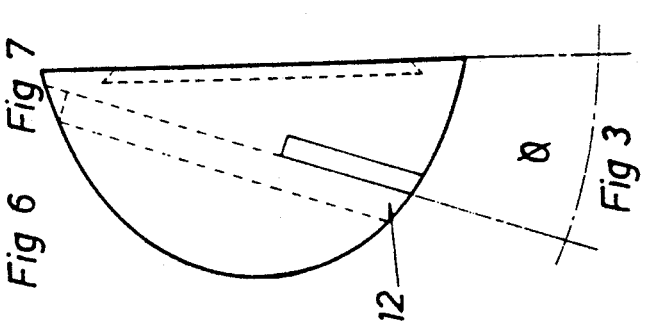

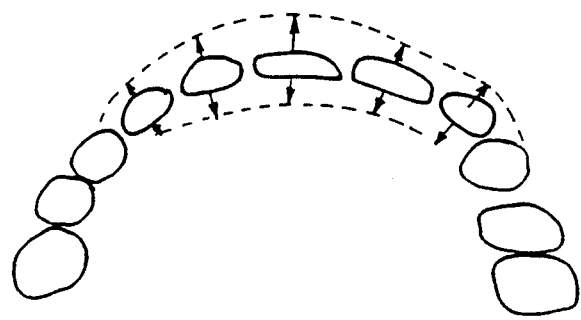
Fig. 8.
Fig. 9.
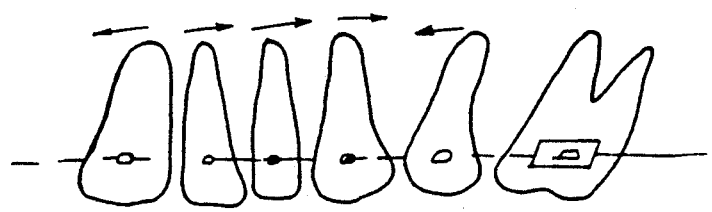

ORTHODONTIC BRACKET AND METHOD

FIELD OF THE INVENTION

The invention relates to orthodontic brackets particularly of the ribbon arch type.

The brackets are of the type which comprise:
(i) A base portion adapted for attachment to the labial surface of a tooth;
(ii) A lock pin receiving portion having a substantially vertical opening extending there through for the lock pin;
(iii) An arch-wire support portion extending substantially normal to the opening defined in Paragraph (ii) and being disposed between the opening and the base portion, hereinafter referred to as a bracket of the type hereinbefore defined.

BACKGROUND OF THE INVENTION

The bracket is of the type for use in the ribbon arch technique. This is a technique which allows an arch-wire to be inserted into the bracket in a vertical direction, as opposed to the edgewise technique in which the bracket has a slot opening horizontally for arch-wire insertion.

With reference to the prior art Specifications known to Applicant, the bracket of Hanson in U.S. Pat. No. 4,698,017, there is disclosed a tie-less bracket for the edgewise technique with a spring clip and uses arch-wires of different cross section.

Klapper U.S. Pat. No. 4,676,746 uses the principles of pre-torquing and pre-angulation and pre-rotation, but requires a three-piece assembly of interchangeable parts.

In my earlier Australian Patent No. 490821, there is disclosed the provision of a base portion having an undercut base which is similar to that disclosed in the Klapper Specification referred to above.

There is also disclosed in U.S. Pat. No. 4,659,309 by Merkel a pre-torqued-preangulated edgewise bracket with a rhomboidal shape. This bracket, together with other edgewise brackets, have sharp corners which are likely to lead to less patient comfort in the mouth and greater resistance to the passage of food.

The Fujita bracket disclosed in U.S. Pat. No. 4,655,708 is a bracket adapted to be applied to the lingual, or tongue, surface of the tooth whereas the present bracket is intended to be applied to the labial or cheek side of the tooth.

The Fujita bracket being a lingually placed bracket has a variable slot position which could include a ribbon arch or vertical insertion presumably from the occlusal side. The Fujita bracket slot has no specific angularity therein and this could lead to inaccuracies in torque angle resulting in a lower standard of finish.

The ribbon arch (Begg brackets demonstrated by Johnston in U.S. Pat. No. 3,408,739 and Kesling in U.S. Pat. No. 3,178,821 illustrate the appliances used in recent years reintroducing the ribbon arch approach to contemporary orthodontics. The main difference between the modern (Begg) technique and the original ribbon arched method is that the modern technique uses a round wire, not a rectangular wire. The Johnston bracket can achieve a lengthening of the archwire slot by the use of an auxiliary device called a "stabilizing bar".

Similarly, Forster discloses in U.S. Pat. No. 4,268,249 a ribbon arch bracket which employs an auxiliary like that of Johnston mentioned above. Forster's bracket can take a rectangular arch-wire, but has no provision for pre-torquing. Kesling in his U.S. Pat. No. 3,178,821 demonstrates a modified ribbon arch bracket, but uses cutaway flanges to allow free tipping mesio-distally, deliberately avoiding any likelihood of restriction of tipping movement, (this movement enables easy correction of tooth crown position, but not root position). The Kesling bracket requires that an auxiliary be used such as the Kesling-Begg spring pin disclosed in British Patent Specification No. 1421601 to achieve correction of root position that is angulation.

This movement must be attained after the crown tipping, mentioned above, occurs.

It is an objective of the present invention to provide an orthodontic bracket of the arch-wire type seeking to overcome some of the abovementioned disadvantages in allowing for smooth rounded edges making for greater patient comfort and less resistance to the passage of food.

It is a further objective to provide an orthodontic bracket wherein the slot angulations are specific for each tooth and can be accurately achieved to the accuracy of a degree than ever could be obtained by adjustments to the prior art (known to me).

It is also an objective to provide an arch-wire slot built in the one-piece bracket.

It is a further objective to provide an orthodontic bracket of the arch-wire type wherein the arch-wire slot is pre-angulated in manufacture and does not require angulation correction.

SUMMARY OF THE INVENTION

There is provided according to the present invention an orthodontic bracket of the type defined herein for adherence to the labial surface of a tooth the bracket including a slot comprising an arch-wire support portion for receipt of a ribbon arch-wire of substantially rectangular cross section adapted to be inserted gingivo-occlusally into the support portion, wherein the base of said support portion is angulated at specific pre-set angles between 0 to 20 degrees to the horizontal axis according to the final desired location of a tooth to which the bracket is to be attached, said bracket being attached to the tooth in a substantially symmetric manner.

Thus the dental operative need only select the requisite bracket for achieving desired tooth movement and mounted on to a tooth to achieve desired angulation movement of a tooth or teeth.

Similarly, there is also provided by the present invention an orthodontic bracket for adherence to a tooth for achieving torque movement of a tooth or teeth wherein the angulation of the arch-wire support portion is pre-set at an angle between 0 to 20 degrees.

Conveniently the arch-wire ribbon is held in place by a substantially vertically directed headed pin slideably mounted in said bracket and adapted to engage said ribbon arch in use.

According to a further aspect of the invention there is provided a method of utilising an orthodontic bracket of the type described herein which method comprises a step of
(i) as part of first and second stages of treatment attaching the bracket having a pre-angulated or tilted slot base to the labial surface of a tooth in a substantially upright disposition so that the arch-wire support portion is tilted from the horizontal with the gingival end of the support portion being arranged to have a round or rectangular arch-wire bear thereon; and (ii) as part of a subsequent treatment stage or subsequent treatment stages forcing a special lock pin down on the arch-wire so that the arch-wire bears on the support portion for most if not all of the distance between the uppermost end and a position adjacent the opening.

Specifically the base of the arch-wire slot can be set at 90 degrees to the lock pin slot or angulated at a specific angle from 90 degrees according to the requirements of the particular tooth. This gives the operator the choice of setting the bracket on the tooth at 90 degrees but simply being able to choose a bracket having a pre-angulated or set angle according to the tooth movement desired.

Conveniently in the third stage of treatment (as defined by Begg) a rectangular arch-wire may be utilised in the setting of a tooth.

A special lock pin with a long head equal to the distance between the arch-wire and the top of the bracket at the gingival end is utilised to maintain the arch-wire seated firmly on the slot base thus an uprighting spring used by most prior art brackets can be dispensed with.

Conveniently the bracket is shaped so as to maximise the length of the arch-wire support portion, thus increasing the length of the lever arm (and hence the turning moment) between the head of the lock pin and the extreme end of the arch-wire support portion or (slot). As the lock pin forces the arch-wire down onto the base of the bracket slot, it induces a distortion in the wire which, as the wire elastically returns to its original shape, moves the tooth to the desired position.

DESCRIPTION OF THE DRAWINGS

The invention will now be described in more detail with reference to the accompanying sketches in which FIG. 1 is a plan view of a bracket for attachment to the surface of the tooth.

FIG. 2 is a bottom plan view of the bracket.

FIG. 3 is a side view showing angulation of the bracket slot in the vertical plane (torque).

FIG. 4 is a front elevation of the bracket showing the angulation of the arch-wire slot base.

FIG. 5 is a rear elevation of the base surface of the bracket attaching to the tooth, showing an escape space for extrusion of excess adhesive.

FIG. 6 is a elevation view of a fixing pin for the third stage of treatment.

FIG. 7 is an elevation view of a fixing pin for a first and second stage of treatment.

FIG. 8 is a schematic view of intended torque movement of teeth according to the invention.

FIG. 9 is a schematic view of teeth for angulation movement according to the invention.

DETAILED DESCRIPTION OF THE INVENTION

Figure 10:
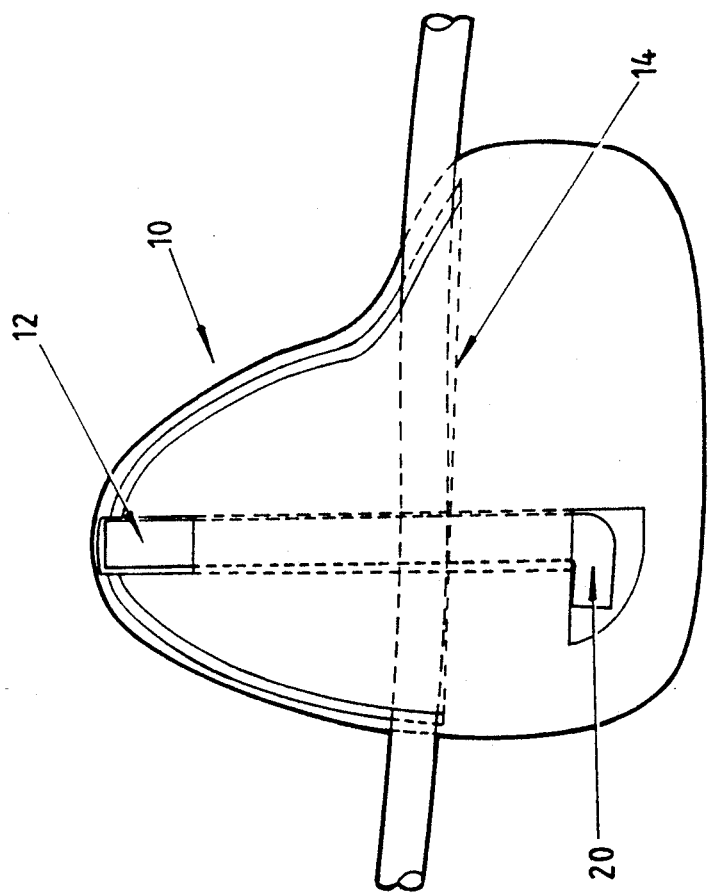
FIG. 10 is a view of a bracket with the arch-wire and lock pin assembled.

With reference to FIGS. 1 to 5 the bracket is depicted in various elevations and comprises a body 10 with an undercut surface portion 13 for adhesive attachment to the labial surface of a tooth by suitable cement. The body includes an arch-wire slot 14 and lock pin slots 12. A ledge portion 11 is provided to accommodate the bent end of the pin in locking engagement on the bracket when in use.

The base of the arch-wire slot may be inclined by an angle $\phi$ in the range of greater than 0 degrees to 20 degrees. The locking pin slot and wall of the arch-wire slot in a vertical plane may be also inclined $\phi$ in the range of greater than 0 degrees to 20 degrees. The angles are pre-set during the manufacture of individual brackets and each bracket can be selected by a dental practitioner according to torque movement or angulatory movement of the tooth or teeth desired for a given patient.

In the third stage of treatment a rectangular cross section arch-wire is used to achieve torque movement as schematically depicted in FIG. 8. In this treatment stage the locking pin may be used simply as a retention pin and accordingly the pin 30 depicted in FIG. 6 is utilised for greater patient comfort.

In the second stage of treatment a round arch-wire may be used to achieve angulatory movement of same teeth as shown in FIG. 9, however, a locking pin 20 as shown in FIG. 6 is used. The locking pin 20 has a head portion 21 extending between the arch wire and the top of the bracket at the gingival end to force the arch-wire against the bottom of the slot 14 bracket to achieve desired angulatory movement of the tooth or teeth.

The longer head portion 21 maintains its position in the slot 12 with the small head portion 22 bearing upon the bracket at the top (gingival) of the lock pin slot. As clearly shown in FIGS. 4 and 5, the bracket configuration is extended in a substantially L form in order to achieve a longer slot base for support of an arch-wire. Thus an increased lever arm is achieved by this configuration, increasing the moment of force available to upright the tooth.

I claim:

1. An orthodontic bracket having a base portion for attachment to the labial surface of a tooth;
    a lock pin receiving portion having a generally vertical lock pin slot extending therethrough for receiving a lock pin;
    an arch-wire support portion extending between said lock pin receiving portion and said base portion, said arch-wire support portion having a generally horizontal arch-wire slot formed therein for receiving an arch-wire, said arch-wire slot having a base angulated at a specific preset angle of between 0 to 20° with respect to a horizontal axis for enabling mesio-distal tipping of the tooth, and said lock pin slot and said arch-wire slot being inclined with reference to a vertical axis for enabling labio-lingual or bucco-lingual torquing of the tooth.

2. An orthodontic bracket as claimed in claim 1 wherein said bracket is generally L-shaped to maximize the length of the slot in the arch-wire support portion for increasing a length of a lever arm between the head of the lock pin and the extreme end of the arch-wire support portion so that as the lock pin forces the arch-wire down onto the base of said slot it induces a distortion in the wire which, as the wire elastically returns to its original shape, moves the tooth to the desired position.

3. An orthodontic bracket as claimed in claim 1 wherein an arch-wire is received in said arch-wire slot and a lock pin is slideably received in said lock pin slot and engaging said arch-wire to hold the arch-wire in place, said lock pin having a head extending between the arch-wire and the top of the bracket at the gingival end, said head forcing said arch-wire against the base of said slot.

4. An orthodontic bracket as claimed in claim 1 wherein said lock pin angle is between about 20 degrees and greater than zero degrees.

5. A method of utilizing an orthodontic bracket having a base portion for attachment to the labial surface of a tooth; a lockpin receiving portion having a generally vertical lock pin slot extending therethrough for receiving a lock pin; an arch-wire support portion extending between said lock pin receiving portion and said base portion, said arch-wire support portion having a generally horizontal arch wire slot for receiving a gingivo-occlusally inserted arch-wire, said arch-wire slot having a base angulated at a specific pre-set angle with reference to a horizontal axis for enabling mesio-distal tipping of the tooth, and said lock pin slot and arch wire slot being inclined with reference to a vertical axis for enabling labio-lingual or bucco-lingual torquing of the tooth, said method comprising the steps of:

(i) as part of first and second stages of treatment, attaching the bracket to the labial surface of a tooth in a substantially upright position and the arch-wire slot angled so that the arch-wire support portion can be tilted mesio-distally from horizontal, inserting an arch-wire into the arch-wire slot and forcing the wire against the tilted slot base to attain a one point contact therewith for tipping the bracket and tooth mesio-distally from horizontal; and (ii) as part of a subsequent third treatment stage, forcing a long headed lock pin into the lock pin slot and against the arch-wire so that the arch-wire bears on the tilted slot base between the gingival end and a position adjacent to the lock pin slot, thereby attaining two point contact for imposing uprighting movement of the tooth.

6. The method as claimed in claim 5 wherein, in the third stage of treatment, a rectangular or ribbon arch-wire utilized in the final setting of the tooth.

* * * * *